(12) United States Patent
Perez et al.

(10) Patent No.: US 8,664,470 B2
(45) Date of Patent: Mar. 4, 2014

(54) MOUSE MODEL OF RETINAL DEGENERATION

(75) Inventors: Victor L. Perez, Pinecrest, FL (US); Joe G. Hollyfield, Shaker Heights, OH (US); Robert G. Salomon, Mayfield Village, OH (US)

(73) Assignees: The Cleveland Clinic Foundation, Cleveland, OH (US); Case Western Reserve University, Cleveland, OH (US)

( * ) Notice: Subject to any disclaimer, the term of this patent is extended or adjusted under 35 U.S.C. 154(b) by 0 days.

(21) Appl. No.: 12/256,274

(22) Filed: Oct. 22, 2008

(65) Prior Publication Data

US 2009/0155243 A1    Jun. 18, 2009

Related U.S. Application Data

(63) Continuation of application No. PCT/US2007/009724, filed on Apr. 23, 2007.

(60) Provisional application No. 60/794,450, filed on Apr. 24, 2006.

(51) Int. Cl.
*A61K 39/395* (2006.01)

(52) U.S. Cl.
USPC .................... 800/9; 800/8; 424/130.1

(58) Field of Classification Search
USPC ............................ 800/18, 14, 8, 21
See application file for complete search history.

(56) References Cited

U.S. PATENT DOCUMENTS

| | | | |
|---|---|---|---|
| 4,873,316 | A | 10/1989 | Meade et al. |
| 5,686,250 | A | 11/1997 | Salomon |
| 7,172,874 | B2 | 2/2007 | Hollyfield et al. |
| 2004/0265924 | A1 | 12/2004 | Hollyfield et al. |
| 2005/0262580 | A1 | 11/2005 | Petrukhin et al. |
| 2008/0160505 | A1 | 7/2008 | Hollyfield et al. |

FOREIGN PATENT DOCUMENTS

| | | |
|---|---|---|
| WO | WO2004-041160 | 5/2004 |
| WO | WO 2004/041160 A2 | 5/2004 |
| WO | WO 2004/041160 A3 | 5/2004 |
| WO | WO2007-127151 | 11/2007 |
| WO | WO2007/127151 A2 | 1/2008 |
| WO | WO2007/127151 A3 | 1/2008 |
| WO | WO 2008/013797 A2 | 1/2008 |
| WO | WO 2008/013797 A3 | 1/2008 |

OTHER PUBLICATIONS

Anand-Apte et al IOVS, (Apr 2004) vol. 45, No. Suppl. 1, pp. U196).*
Schunk et al ILAR Journal, 2005, 46(3), 241-257.*
Qin et al Journal of Inflammation Research, 2008, 49-65.*
den Hurk et al Immunol Rev. 2004; 199:113-25.*
Hollyfield et al Nature Medicine,. 2008, 14, 194-198.*
Notification of Transmittal of the International Search Report and the Written Opinion of the International Searching Authority, or the Declaration for International Application No. PCT/US2007/009724, mailed Jul. 11, 2007.
Notification Concerning Transmittal Copy of the International Preliminary Report on Patentability for International Application No. PCT/US2007/009724, mailed Nov. 6, 2008.
Ambati, J., et al., "An Animal Model of Age-Related Macular Degeneration in Senescent Ccl-2- or Ccr-2-deficient Mice", *Nature Medicine*, 9(11):1390-1397 (Nov. 2003).
Besharse, J.C. & Hollyfield, J.G., "Turnover of Mouse Photoreceptor Outer Seqments in Constant Light and Darkness", *Invest. Ophthalmol. Vis. Sci.*, 18:1019-1024 (Oct. 1979).
Crabb, J. et al., "Drusen Proteome Analysis: An Approach to the Etiology of Age-Related Macular Degeneration", *Proc Natl Acad Sci* (USA), 99(23):14682-14687 (Nov. 12, 2002).
Dobi, E.T., et al., "A New Model of Experimental Choroidal Neovascularization in the Rat", *Arch. Ophthalmol.*, 107:264-269 (Feb. 1989).
Gu, X., et al., "Carboxyethylpyrrole Protein Adducts and Autoantibodies, Biomarkers for Age-Related Macular Degeneration", *J. Biol. Chem.*, 278(43):42027-42035 (Oct. 24, 2003).
Hollyfield, J.G., et al., "Identification of an Inflammatory Signal from the Outer Retina Causing Age-Related Macular Degeneration", *Association for Research in Vision and Ophthalmology Meeting*, Fort Lauderdale, Florida, Apr. 29-May 4, 2007.
Hollyfield, J.G., et al., "Proteomic Approaches to Understanding Age-Related Macular Degeneration", *Adv. Exp. Med. Biol.*, 533:83-89 (2003).
Parker, D.C., "T Cell-Dependent B Cell Activation", *Ann Rev Immunol.*, 11:331-360 (1993).
Percopo, C.M., et al., "Cytokine-Mediated Activation of a Neuronal Retinal Resident Cell Provokes Antigen Presentation", *J Immunol.*, 145:4101-4107 (Dec. 15, 1990).
Roth, F., et al., "Keypathophysiologic Pathways in Age-Related Macular Disease," *Graefe's Arc. for Clin. and Exp. Ophthal.*, 242(8):710-716 (Aug. 10, 2004).
Ni, J. et al., "Plasma Protein Pentosidine and Carboxymethyllysine, Biomarkers for Age-related Macular Degeneration," Molecular & Cellular Proteomics (2009).

* cited by examiner

*Primary Examiner* — Anoop Singh
(74) *Attorney, Agent, or Firm* — Fish & Richardson P.C.

(57) ABSTRACT

The invention is directed to a method of producing a non-human mammal having one or more pathological characteristics of retinal degeneration and/or age-related macular degeneration. In particular, the invention provides a method of producing a non-human mammal having age-related macular degeneration (AMD). The invention is also directed to non-human animals produced by the methods described herein. Methods of identifying an agent for use in inhibiting one or more pathological characteristics of retinal degeneration and/or AMD is also encompassed by the invention. Also provided is a method of treating AMD in an individual in need thereof comprising, administering to the individual an agent identified herein.

7 Claims, 8 Drawing Sheets

Carboxyethylpyrrole Chemistry

Oxidative fragmentation of docasohexaenoic acid (DHA)

DHA 4-hydroxy-7-oxohept-5-enoic acid (HOHA)

Carboxyethylpyrrole (CEP)

FIG. 8

The fragmentation event specified generates HOHA, a seven carbon fragment that can only be derived from DHA. HOHA covalently interacts with the epsilon amino group in protein to produce the hapten CEP.

FIG. 9

MOUSE MODEL OF RETINAL DEGENERATION

RELATED APPLICATION(S)

This application is a continuation of International Application No. PCT/US2007/009724, which designated the United States and was filed on Apr. 23, 2007, published in English, which claims the benefit of U.S. Provisional Application No. 60/794,450, filed on Apr. 24, 2006. The entire teachings of the above applications are incorporated herein by reference.

GOVERNMENT SUPPORT

The invention was supported, in whole or in part, by a grant GM 21249 (RGS) from the U.S. National Institute of Health. The Government has certain rights in the invention.

BACKGROUND OF THE INVENTION

The role of oxidatively modified (e.g., by adduction of an oxidatively truncated lipid) self proteins in autoimmune diseases has not been studied. An example of such an autoimmune disease is age related macular degeneration (AMD). AMD is the leading cause of blindness in the elderly population in developed countries. Over a third of those over the age of 75 currently have some form of this disease. Slowing or preventing the progression of AMD is an urgent public health goal. The role of inflammation is believed to be one of the crucial first steps that occur early on in patients that will eventually develop blinding AMD. In the USA, the prevalence of AMD in Medicare beneficiaries age 65 or older increased from 5.0% to 27.1% between 1991 and 1999. Assuming the US population 65-years and older grows as projected to reach 70.3 million by 2030, AMD cases in this country will soon exceed 20 million. The use of intravitreal steroids as an adjuvant in the treatments of late stage AMD support the role of inflammatory responses in retinal degeneration. Presently, there are no immunosuppressive therapies used to prevent AMD.

Therefore, a better understanding of immune responses in autoimmune diseases, such as AMD, can lead to the development of diagnostic and therapeutic modalities that can be used early on before irreversible damage occurs.

SUMMARY OF THE INVENTION

The invention is directed to a method of producing a non-human mammal having one or more pathological characteristics of retinal degeneration. The method comprises administering a composition comprising an oxidatively modified protein (e.g., self protein) to a non-human mammal; and maintaining the non-human mammal under conditions in which one or more pathological characteristics of retinal degeneration develops in the non-human mammal, thereby producing a non-human mammal having one or more pathological characteristics of retinal degeneration.

The invention is also directed to a method of producing a non-human mammal having one or more pathological characteristics of age related macular degeneration (AMD). The method comprises administering a composition comprising carboxyethylpyrrole (CEP) modified serum albumin to a non-human mammal on day 0, day 10 and day 60. The non-human mammal is maintained under conditions in which one or more pathological characteristics of AMD develops in the non-human mammal, thereby producing a non-human mammal having one or more pathological characteristics of AMD.

Also encompassed by the invention is a method of producing a non-human mammal having age-related macular degeneration (AMD). The method comprises administering a composition comprising carboxyethylpyrrole (CEP) modified serum albumin to a non-human mammal on day 0 and day 10; and maintaining the non-human mammal under conditions in which AMD develops in the non-human mammal, thereby producing a non-human mammal having AMD.

The invention is also directed to non-human animals produced by the methods described herein.

A method of identifying an agent for use in inhibiting one or more pathological characteristics of retinal degeneration is also encompassed by the invention. The method comprises administering, an agent to be assessed to the non-human mammal described herein. Whether one or more pathological characteristics of retinal degeneration is inhibited in the non-human mammal is determined and compared to a control. If the one or more pathological characteristics of retinal degeneration is inhibited in the non-human mammal compared to a control, then the agent can be used to inhibit one or more pathological characteristics of retinal degeneration.

The invention is also directed to a method of identifying an agent for use in inhibiting age related macular degeneration (AMD). The method comprises administering an agent to be assessed to the non-human mammal described herein. Whether AMD is inhibited in the non-human mammal is determined and compared to a control, wherein if AMD is inhibited in the non-human mammal compared to a control, then the agent can be used to inhibit AMD.

A method of treating AMD in an individual in need thereof comprising, administering to the individual an agent identified herein is also provided.

BRIEF DESCRIPTION OF THE DRAWINGS

FIGS. 6A-6C show micrographs of retina from mice (FIG. 6A and FIG. 6C) recovered 12 months following immunization with CEP-MSA in complete Freund's adjuvant (FA) followed by a boost 10 days after the initial immunization with CEP-MSA in incomplete FA; in FIG. 6A, arrows on the lower border of the micrograph indicate the localization of debris-like material present below the RPE; FIG. 6B is from a 78 year old human female AMD donor eye containing soft drusen between the RPE and Bruch's membrane (at the level of the arrow on right of image).

DETAILED DESCRIPTION OF THE INVENTION

AMD is a progressive, multifactorial, polygenic disease with poorly understood etiology. Early stages of the disease are typically termed "dry" AMD and associated with the macular accumulation of extracellular deposits (drusen) below the retinal pigment epithelium (RPE) on Bruch's membrane of the retina. Geographic atrophy develops in the later stages of dry AMD and is characterized by macular loss of RPE and photoreceptor cells. Advanced stage disease or "wet" AMD is characterized by choroidal neovascularization. Oxidative damage and vascular factors are considered important insults in the pathogenesis of age related macular degeneration (AMD). However, recent reports demonstrate that drusen and surrounding retinal pigmented cells (RPE) contain immunoreactive components of the immune system that activate, complement and induce immune complex deposition.

Figure 9:
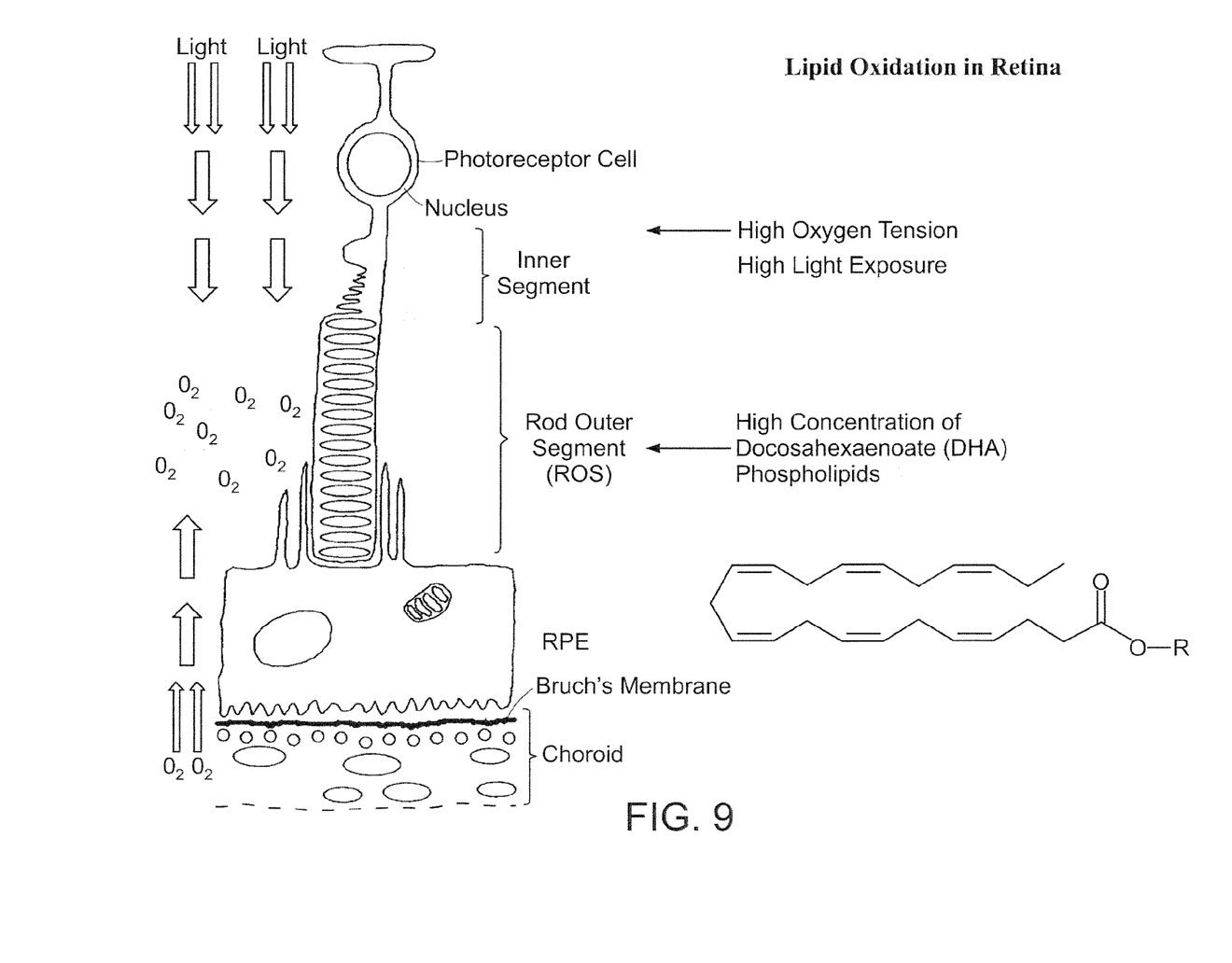
FIG. 9 is a schematic illustrating lipid oxidation in the retina.

Despite the association between the components of drusen and the immune system, little is known about the events that trigger the development of AMD. Described herein is the investigation of whether the development of an immune response and inflammation to factors in Bruch's membrane and RPE cells is an important step in the development of AMD. The invention is based, in part, on the discovery that an inflammatory response against a self, oxidatively modified (e.g., by adduction of an oxidatively truncated lipid) protein (e.g., serum albumin) is likely an initial step in the induction of an autoimmune response that leads to the development of AMD. Carboxyethylpyrrole (CEP) protein modifications, uniquely generated from oxidation of docosahexaenoate-containing lipids are more abundant in ocular tissues from AMD than normal donors and are concentrated in Bruch's membrane, the blood retinal barrier (see FIG. 9). The outer segments of the photoreceptors contain high concentrations of polyunsaturated fatty acids (PUFAs), especially DHA, in the membranes and are exposed to relatively high oxygen tension, close to that found in arterial blood. The photooxidative environment in the retina and the DHA rich photoreceptor outer segments provide a ready source of reactive oxygen species for generating oxidative modifications. A high level of mitochondrial activity required to maintain membrane potentials in photoreceptor cells is also a likely source of free radicals that can promote autoxidative fragmentation of DHA-containing membrane phospholipids. PUFAs undergo oxidation in the presence of oxygen or oxygen derived radical species, and elevated levels of CEP protein adducts and CEP autoantibodies are present in AMD plasma (Gu, X. et al. (2003) *J. Biol. Chem.*, 273.42027-42035; U.S. Published Application No. 2004/0265924 A1). One example of a CEP modified protein is CEP modified serum albumin. Auto-antibodies against CEP-Human Serum Albumin (HSA) have been detected in patients with AMD.

As shown herein, peripheral immunogeneic immunization of a non-human mammal (e.g., a murine model) with one or more CEP protein adducts (e.g., CEP-mouse serum albumin (CEP-MSA) in complete freund adjuvant (CFA)) can induce an adaptive immune response comprised of an antigen specific T cell response and the production of anti-CEP-MSA auto-antibodies that results in the destruction of tissue where CEP is highly localized. It is likely that the retinal photoreceptors, brain and other sites where CEP adducts are present are affected. Presently, there are no in vivo animal models to study the role of early and late inflammatory responses in retinal degeneration. There is only one model described in the use of mice that lack MCP-1 ligand or receptor, and these take 9 months to 1 year to develop disease (Ambati, et al, *Nature Medicine* 9:1390-1397 (2003)). The other model used to study choroidal neovascularization observed in the late stages of AMD is laser induced choroidal damage and the results obtained utilizing this model can be affected by the wound healing response associated with the laser burn (Dobi, et al., *Arch. Opthalmol.*, 107:264-269 (1989)). One embodiment of the invention described herein is a model of spontaneous retinal degeneration that results from an immune specific response to CEP adducts present in retinal photoreceptors in a relatively fast fashion. The present invention is also directed to a method of producing a model of spontaneous retinal degeneration that results from an immune specific response to CEP adducts present in retinal photoreceptors in a relatively fast fashion.

Thus, the studies described herein demonstrate that an autoimmune response against oxidatively modified proteins (e.g., self protein; non-self protein) can be generated in vivo. Accordingly, the present invention is directed to methods of producing a nonhuman animal model of an autoimmune response, non-human animals produced by the methods of the present invention (e.g., non-human models of autoimmune disease such as AMD) and use of the non-human animals (e.g., to identify agents that inhibit one or more pathological characteristics of retinal degeneration and/or AMD).

In particular embodiments, the invention provides for methods of producing a non-human animal model of an autoimmune response to oxidatively altered self protein. In this embodiment, the method comprises administering to (immunizing) a non-human animal with a composition (first composition) comprising an (one or more) oxidatively modified self protein, and optionally an adjuvant. The non-human mammal is then administered (challenged with) one or more compositions (e.g., a second composition, a third composition, a fourth composition, etc.) comprising an oxidatively modified self protein. The non-human animal is maintained under conditions in which an autoimmune response develops in the non-human animal. The second, third, fourth etc, composition can be the same as, similar to, or different from the oxidatively modified protein in the first composition. For example, the second, third, fourth etc, composition can comprise a different oxidatively modified protein (e.g., an oxidatively modified self protein or an oxidatively modified non-self protein that differs from the oxidatively modified protein of the first composition); and/or optionally, the second, third, fourth etc, composition can comprise an adjuvant that differs from the adjuvant of the first composition. In a particular embodiment, the second, third, fourth etc, composition is the same as, or similar to, the oxidatively modified protein in the first composition.

As used herein, the term "animal" includes mammals, as well as other animals, vertebrate and invertebrate (e.g., birds, fish, reptiles, insects (e.g., *Drosophila* species), mollusks (e.g., *Aplysia*). In a particular embodiment, the animal is a mammal. The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and primates (e.g., monkeys, chimpanzees), rodents (e.g., rats, mice, guinea pigs) and ruminants (e.g., cows, pigs, horses).

As indicated herein the non-human animal is administered multiple doses of the composition. That is, the animal can be administered a first composition, a second composition, a third composition, a fourth composition, a fifth composition, etc. In one embodiment, the non-human mammal is administered the composition on day 0, day 10 and/or day 60. In another embodiment, the non-human mammal is administered the composition on day 0 and/or on day 10. Other combinations of administrations can be used and can depend on a variety of factors such as the oxidatively modified self protein being administered to, and/or the particular autoimmune response being developed in the animal, which is apparent to those of skill in the art.

As shown herein an "oxidatively modified protein", an "oxidatively modified self protein" or an "oxidatively modified non-self protein" for use in the methods of the invention includes a carboxyethylpyrrole (CEP) modified protein (also referred to herein as a CEP protein adduct). Carboxyethylpyrrole (CEP), a unique protein modification derived from the oxidation of docosahexaenoate (DHA)-containing lipids, was found to be more abundant in AMD compared to normal ocular tissues (Crabb, J. W., et al. (2002) *Proc Natl Acad Sci USA* 99, 14682-7) and was localized in Bruch's membrane between the blood-bearing choriocapillaris and RPE. Carboxyethylpyrrole (CEP) protein adducts belong to a family of 2-(ω-carboxyalkyl)pyrrole adducts generated from the oxidation of polyunsaturated fatty acids (PUFA) (see Gu et al., *J. Biol. Chem.*, 278(43):42027-42035 (2003) and U.S. Published Application No. 2004/0265924, both of which are incorporated herein by reference). Docosahexaenoic acid (DHA) gives rise to 2-(ω-carboxyethyl)pyrrole adducts, by oxidative cleavage to 4-hydroxy-7-oxohept-5-enoic acid (HOHA) and reaction of the HOHA with protein (FIG. 12). HOHA can form an adduct with one or more primary amino groups of a peptide (e.g., a dipeptide) or protein resulting in a CEP epitope that is referred to as CEP-peptide or CEP-protein adducts, respectively. For example, HOHA can form an adduct with, or on, proteins such as albumin, and fragments thereof. CEP epitopes can also be generated by the reaction of HOHA with the primary amino group of ethanolamine phospholipids that are referred to as ethanolamine phospholipid CEP adducts. Also phospholipids containing an HOHA residue can form CEPs through reaction with primary amino groups of biomolecules such as proteins followed by phospholipolysis of the initially formed CEP phospholipid ester derivative. Thus, an "oxidatively modified protein" for use in the methods of the present invention can also include other 2-(ω-carboxyalkyl)pyrrole protein adducts which when administered to an animal, and subsequently used to challenge the immune system of the animal, results in the production of a non-human animal model of an autoimmune response to the oxidatively modified self protein. For example, other 2-(ω-carboxyalkyl)pyrrole protein adducts include carboxypropylpyrroles, carboxyheptylpyrroles, levuglandin and isolevuglandin (U.S. Pat. No. 5,686,250 and U.S. Pat. No. 7,172,874 which are incorporated herein by reference).

Although the invention is described in the exemplification in terms of an oxidatively modified self protein, it is reasonable to expect that an immune response to CEP epitopes can be generated using any suitable immunogenic entity that presents a CEP to the immune system of an animal. That is, the nonhuman animals of the invention can be generated using any suitable CEP epitope capable of generating an immune response that is directed to a (one or more) CEP-modified self protein. In a particular embodiment, the nonhuman animals of the invention can be generated using any suitable CEP epitope capable of generating antibodies that react (e.g., cross react, specifically bind, are directed against, have binding specificity for) one or more CEP-modified self proteins.

A variety of proteins (polypeptides) which can carry (are capable of carrying) a 2-(ω-carboxyalkyl)pyrrole such as CEP can be used in the methods of the present invention. In one embodiment, the protein is a self protein or portion thereof which forms or carries (is capable of forming or carrying) a 2-(ω-carboxyalkyl)pyrrole and which generates (is capable of generating) an immune response that is directed to a (one or more) CEP-modified self protein. As used herein a "self protein" is any protein present in, or normally present in, an animal and which can form an adduct with a 2-(ω-carboxyalkyl)pyrrole. An example of a self protein that can be used in the methods described herein is a serum protein. Specific examples of self proteins which can be used in the methods of the invention include albumin, ovalbumin, cystallin, ceruloplasmin, fibronectin, serum amyloid P, actinin, beta B1 and other circulating protein and/or peptides. In a particular embodiment, the oxidative modified self protein is CEP-mouse serum albumin (CEP-MSA).

In another embodiment, the protein is a non-self protein or portion thereof which forms or carries a 2-(ω-carboxyalkyl)pyrrole and generates an immune response that is directed to a (one or more) CEP-modified self protein. As used herein, a "non-self protein" is any protein that is not normally present in the animal (a foreign or exogenous protein) and which can form an adduct with a 2-(ω-carboxyalkyl)pyrrole. Non-self proteins include self proteins that have been modified (and thus, as modified are not normally present in an animal) using methods known to those of skill in the art. A specific example of a self protein which can be used in the methods of the invention includes keyhole limpet hemocyanin (KLH).

Thus, an oxidatively modified self protein, non-self protein or portion thereof can be modified to incorporate a 2-(ω-carboxyalkyl)pyrrole and administered to the animal for use in the methods of the invention. The portion of the self protein, non-self protein or portion thereof can comprise a portion which is capable of stimulating an immune response either alone or as modified to incorporate a 2-(ÿ-carboxyalkyl)pyrrole in an animal. One or more portions of the protein (peptide) can be used which can be contiguous or non-contiguous portions of the protein. For example, the portion can be an antigenic portion (e.g., one or more portions which include one or more epitopes of a protein) of a self protein.

The amount of a 2-(ω-carboxyalkyl)pyrrole such as CEP adducted to a protein or a portion thereof for use in the methods of the invention typically range from about 5 moles to about 15 moles 2-(ω-carboxyalkyl)pyrrole per about 1 mole or about 2 moles of protein or portion thereof. In another embodiment, the range is from about 6 moles to about 12 moles 2-(ω-carboxyalkyl)pyrrole per mole of protein or portion thereof. In particular embodiments, about 5, 6, 7, 8, 9, 10, 11, 12, 13, 14 or 15 moles of a 2-(ω-carboxyalkyl)pyrrole is adducted to about 1 mole of a protein or portion thereof.

The dosage of oxidatively modified self protein typically administered to a non-human animal in the methods of the invention typically range from about 10 μg to about 200 μg, from about 20 μg to about 150 μg, from about 30 μg to about 100 μg, and from about 40 μg to about 50 μg. As will be apparent to one of skill in the art, the dosage administered will depend upon factors such as the period of time over which the oxidatively modified protein is to be administered.

As shown herein the oxidatively modified self protein can be administered with an adjuvant. Examples of suitable adjuvants that can be used in the methods include complete Freund's adjuvant (CFA), incomplete Freund's adjuvant (IFA), *Bordetella pertussis* and alum.

Any variety of methods can be used to administer the oxidatively modified self protein to the non-human animal. As know to one of skill in the art, the route of administration will depend upon a variety of factors, such as the way in which the oxidatively modified self protein has been formulated for delivery. Examples of suitable routes of administration include subcutaneous, intravenous, intradermal, intramuscular, intraperitoneal, intraocular, topical, oral and intranasal. Other suitable methods of introduction can also include gene therapy, rechargeable or biodegradable devices, particle acceleration devises ("gene guns") and slow release polymeric devices.

2-(ω-carboxyalkyl)pyrrole adducted protein such as CEP adducted protein can be recognized by T cells and an antibody response can be elicited after immunization with the CEP adducted protein (e.g., a CEP adducted serum protein such as CEP-MSA). Moreover, the generation of such an autoimmune response results in tissue damage of retinal photoreceptors where the CEP antigen is highly localized. The data described herein demonstrate an autoimmune T and B cell response to oxidative modified self proteins that results in tissue specific disruption. In particular embodiments, the present invention provides a model in which the development of spontaneous immune mediated retinal degeneration can be used to study the role of inflammation in autoimmune diseases, such as AMD and other autoimmune diseases.

In one embodiment, the present invention provides a method of producing a non-human mammal having one or more pathological characteristics of retinal degeneration. The method comprises administering a composition comprising an oxidatively modified self protein to a non-human mammal. The non-human mammal is maintained under conditions in which one or more pathological characteristics of retinal degeneration develops in the non-human mammal, thereby producing a non-human mammal having one or more pathological characteristics of retinal degeneration.

Pathological characteristics of retinal degeneration include the presence of anti-2-(ỹ-carboxyalkyl)pyrrole antibodies (e.g., anti-CEP antibodies), lysis of retinal pigmented epithelium (RPE) cells, invading inflammatory cells in the interphotoreceptor matrix (IPM), focal loss of RPE, sub-RPE deposits, drusen, complement deposition in Bruch's membrane, RPE lysis/atrophy, photoreceptor loss, macular degeneration, geographic atrophy, macular edema, diabetic retinopathy or a combination thereof in the non-human animal. As one of skill in the art will appreciate, a particular combination of pathological characteristics of retinal degeneration can also lead to age-related macular degeneration (AMD) in the animal.

Thus, the invention also provides a method of producing a non-human mammal having one or more pathological characteristics of AMD. The method comprises administering a composition comprising an oxidatively modified self protein to a non-human mammal. The non-human mammal is maintained under conditions in which one or more pathological characteristics of AMD develops in the non-human mammal, thereby producing a non-human mammal having one or more pathological characteristics of AMD.

In another embodiment, the invention provides a method of producing a non-human mammal having AMD. In this embodiment, the method comprises administering a composition comprising carboxyethylpyrrole (CEP) modified serum albumin to a non-human mammal on day 0 and day 10. The non-human mammal is maintained under conditions in which AMD develops in the non-human mammal, thereby producing a non-human mammal having AMD. The ADM which develops in the non-human animal can be, for example, dry AMD or wet AMD.

Conditions under which the non-human animals of the invention are maintained so that pathological characteristics of retinal degeneration and/or AMD develop will be apparent to one of skill in the art and includes normal animal room illumination (e.g., 12 hours in light/12 hours in darkness).

Whether the non-human animal develops pathological characteristics of retinal degeneration and/or AMD can be determined using skills known in the art. For example, a fundus examination and/or a histological analysis, can be performed to identify pathological characteristics of retinal degeneration and/or AMD in the non-human animal. Specifically, focal loss of RPE can be observed in a fundus examination. The loss of RPE can be evaluated using histology and is evident by the focal absence of RPE cells resulting in an interrupted RPE with only Bruch's membrane present.

It is also reasonable to expect that the non-human animals of the invention can be produced using T cells that are specific for the CEP-modified self protein. That is, T cells that are specific for the CEP-modified self protein are isolated (e.g., purified, substantially purified, partially purified) from the non-human animals produced as described herein. The isolated T cells are then administered to a non-human animal that does not have one or more pathological characteristics of retinal degeneration (a normal, non-human animal). The animal is maintained under conditions in which the T cells attack CEP in the animal which results in the manifestation of one or more pathological characteristics of retinal degeneration in the animal.

The invention also encompasses non-human animals produced by the methods described herein. In one embodiment, the non-human animal is a non-human animal model of an autoimmune response to oxidatively altered self protein produced by the methods of the present invention (e.g., non-human models of autoimmune disease). In other embodiments, the non-human animal has one or more pathological characteristics of retinal degradation and/or one or more pathological characteristics of AMD. In a particular embodiment, the non-human animal is a non-human animal model of AMD.

AMD is the leading cause of blindness in the elderly population in developed countries. Over a third of those over the age of 75 currently have some form of this disease. Slowing or preventing the progression of AMD is an urgent public health goal. The role of inflammation is believed to be one of the crucial first steps that occur early on in patients that will eventually develop blinding AMD. Therefore, the understanding of immune responses in autoimmune diseases such as AMD lead to the development of diagnostic and therapeutic modalities that can be used early on before irreversible damage occurs. Presently, there are no in vivo models of immune mediated AMD. Therefore, the present invention provides unique models which can be used in a variety of applications. Examples of such applications are described below in terms of CEP, however, one of skill in the art will appreciate that the application can apply to other 2-(ω-carboxyalkyl)pyrroles as well as protein modifications by other reactive oxidatively damaged lipids such as levuglandins and isolevuglandins. Thus, the non-human animal models described herein can be used in methods to identify and/or develop:

inflammatory systemic signals of early inflammatory responses in pre-retinal degeneration or other autoimmune diseases associated with anti-CEP response;

inflammatory systemic signals of inflammatory responses during the generation of retinal degeneration or other autoimmune diseases associated with anti-CEP response;

inflammatory local signals of early inflammatory responses in pre-retinal degeneration or other autoimmune diseases associated with anti-CEP response;

inflammatory local signals of inflammatory responses during the generation of retinal degeneration or other autoimmune diseases associated with anti-CEP response;

immune related genes associated with increased risk of developing retinal degeneration or other autoimmune diseases associated with anti-CEP response;

inflammatory markers that can be used to monitor systemic immunosuppression of CEP mediated immune responses;

biological response modifiers to block CEP immune responses in retinal degenerations and other autoimmune diseases (systemic and local);

pathogenic CEP specific T cell clones that can be used to develop and/or screen biological response modifiers or pharmaceutical drugs to block CEP immune responses in retinal degenerations and other autoimmune diseases;

regulatory CEP specific T cell clones that can be used to develop and/or screen biological response modifiers or pharmaceutical drugs to induce immune CEP specific protection in retinal degenerations and other autoimmune diseases;

CEP specific T cell clones that could be used to generate peptides to generate or induce an immune response (e.g., protective vaccines) to prevent early immune mediated retinal damage and protect patients at risk of developing AMD and other autoimmune diseases;

the role of other oxidative modifications to a variety of self proteins and the association of these with the development of AMD and other autoimmune diseases;

agents (e.g., protein, peptides, oligonucleotides, small molecules) can be administered to the in vivo models described herein to identify those that can be used to treat (e.g., ameliorate the effects of) and/or inhibit (e.g., partially, completely) autoimmune diseases.

Accordingly, the present invention is also directed to a method of identifying an agent for use in inhibiting one or more pathological characteristics of retinal degeneration. The method comprises administering an agent to be assessed to the non-human mammal having one or more pathological characteristics of retinal degeneration and determining whether one or more pathological characteristics of retinal degeneration is inhibited in the non-human mammal compared to a control. If the one or more pathological characteristics of retinal degeneration is inhibited in the non-human mammal compared to a control, then the agent can be used to inhibit one or more pathological characteristics of retinal degeneration.

The present invention also encompasses a method of identifying an agent for use in inhibiting AMD. The method comprises administering an agent to be assessed to the non-human mammal having one or more pathological characteristics of AMD and determining whether age related macular degeneration is inhibited in the non-human mammal compared to a control. If age related macular degeneration is inhibited in the non-human mammal compared to a control, then the agent can be used to inhibit age-related macular degeneration.

A suitable control for use in the methods of the invention will be apparent to one of skill in the art. For example, the control can be a wild type non-human animal which is the same species as the non-human animal having one or more pathological characteristics of retinal degeneration and/or AMD and to which the agent to be assessed has not been administered. Alternatively, the control can be a non-human animal having one or more pathological characteristics of retinal degeneration and/or AMD to which the agent to be assessed has not been administered.

The terms, "inhibits" and "treat" as used herein, refer not only to ameliorating symptoms associated with the condition or disease, but also preventing or delaying the onset of the condition or disease, and/or lessening the severity or frequency of symptoms of the condition or disease.

The agents identified herein can inhibit (partially, completely) activity and/or formation of CEP protein adducts in an individual. For example, an agent that inhibits CEP protein adducts can be administered in order to decrease and/or prevent the activity and/or formation of CEP protein adducts.

An agent that inhibits a (one or more) CEP protein adduct is an agent or compound that inhibits the activity and/or formation (expression) of a CEP protein adduct, as described herein (e.g., a CEP protein adduct antagonist). An agent that inhibits a CEP protein adduct can alter CEP protein adduct activity or CEP protein adduct formation by a variety of means. The inhibition can be partial or complete inhibition of CEP protein adduct activity and/or formation. In addition, the agent can inhibit the CEP protein adduct directly (specifically interact) or indirectly (non-specifically interact).

For example, the agent identified in the methods of the present invention can inhibit one or more biological activities of CEP protein adducts. In one embodiment, the agent binds to all or a portion (e.g., a portion of the CEP protein adduct; the CEP portion of the CEP protein adduct; the protein or peptide portion of the CEP protein adduct) of the CEP protein adduct under conditions in which the activity of the CEP protein adduct is inhibited.

Alternatively, the agent identified in the methods of the present invention can inhibit formation of the CEP protein adduct. For example, the agent can prevent CEP protein adducts from forming, and/or hydrolyze CEP protein adducts that have previously formed, regenerating the primary amino group found in the unmodified biomolecule. The agent can also interact with the CEP protein adduct or portion thereof after CEP protein adducts have formed, for example, under conditions in which the pyrrole moiety of the CEP and the protein of the CEP protein adduct is disrupted. In particular embodiments, the agent cleaves the CEP group from the protein.

Examples of agents which can inhibit receptor-mediated effects of CEP protein adducts include the following: nucleic acids, fragments or derivatives thereof and vectors comprising such nucleic acids (e.g., a nucleic acid molecule, cDNA, and/or RNA); polypeptides; peptidomimetics; fusion proteins or prodrugs thereof; antibodies; ribozymes; aptamers; small molecules; and other compounds that inhibit CEP protein adduct activity and/or formation.

In a particular embodiment, the agent or compound that inhibits CEP protein adduct activity and/or formation is an antibody (e.g., a polyclonal antibody; a monoclonal antibody). For example, antibodies that bind all or a portion of one or more CEP protein adducts and that inhibit CEP protein adduct activity can be used in the methods described herein (Gu et al., *J. Biol. Chem.*, 278(43):42027-42035 (2003) and U.S. Application No. 2004/0265924, both of which are incorporated herein by reference). In a particular embodiment, the antibody is a purified antibody. The term "purified antibody" as used herein refers to immunoglobulin molecules and immunologically active portions of immunoglobulin molecules, i.e., molecules that contain an antigen binding site that selectively binds all or a portion (e.g., a biologically active portion) of a CEP protein adduct. A molecule that selectively binds to a CEP protein adduct is a molecule that binds to a CEP protein adduct or a fragment thereof, but does not substantially bind other molecules in a sample (e.g., a biological sample that naturally contains the CEP protein adduct). Preferably the antibody is at least 60%, by weight, free from proteins and naturally occurring organic molecules with which it naturally associated. More preferably, the antibody preparation is at least 75% or 90%, and most preferably, 99%, by weight, antibody. Examples of immunologically active portions of immunoglobulin molecules include F(ab) and F(ab')$_2$ fragments that can be generated by treating the antibody with enzymes such as pepsin or papsain, and single chain FV (scFV) fragments.

The term "monoclonal antibody" or "monoclonal antibody composition," as used herein, refers to a population of antibody molecules that contain only one species of an antigen binding site capable of immunoreacting with a particular epitope of a CEP protein adduct of the invention. A monoclonal antibody composition thus typically displays a single binding affinity for a particular CEP protein adduct of the invention with which it immunoreacts.

Polyclonal antibodies can be prepared using known techniques such as by immunizing a suitable subject with a desired immunogen, e.g., a CEP protein adduct or fragment thereof. The antibody titer in the immunized subject can be monitored over time by standard techniques, such as with an enzyme linked immunosorbent assay (ELISA) using immobilized polypeptide. If desired, the antibody molecules directed against the CEP protein adduct can be isolated from the mammal (e.g., from tissue, blood) and further purified by well-known techniques, such as protein A chromatography to obtain the IgG fraction.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

The present invention is also directed to a method of treating age-related macular degeneration in an animal in need thereof comprising, administering to the individual an agent identified in the methods described herein.

The agents which inhibit CEP protein adducts are administered in a therapeutically effective amount (i.e., an amount that is sufficient to treat or inhibit the disease or condition, such as by ameliorating symptoms associated with the disease or condition, preventing or delaying the onset of the disease or condition, and/or also lessening the severity or frequency of symptoms of the disease or condition). The amount that will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

The methods of the present invention can be used to treat any suitable animal (individual). In one embodiment, the animal is a primate. In a particular embodiment, the individual is a human.

The agents (e.g., therapeutic compound) can be delivered in a composition, as described above, or by themselves. They can be administered systemically, or can be targeted to a particular tissue. The therapeutic compounds can be produced by a variety of means, including chemical synthesis; recombinant production; in vivo production (e.g., a transgenic animal, such as U.S. Pat. No. 4,873,316 to Meade et al.), for example, and can be isolated using standard means such as those described herein. A combination of any of the above methods of treatment can also be used.

The compounds for use in the methods described herein can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy, rechargeable or biodegradable devices, particle acceleration devises ("gene guns") and slow release polymeric devices. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In another embodiment, the invention is directed to agents that inhibit CEP protein adducts for use as a medicament in therapy. For example, the agents identified herein can be used in the treatment of optic nerve damage. In addition, the agents identified herein can be used in the manufacture of a medicament for the treatment of AMD.

EXEMPLIFICATION

CEP Immunization and the Development of an AMD-Like Pathology in the Mouse

A. Identification of an Inflammatory Signal from the Outer Retina Causing Age-Related Macular Degeneration.
Purpose: To experimentally demonstrate the linkage between oxidative modifications of proteins in the outer retina, their recognition by the immune system and the vulnerability of the outer retina to immune attack leading to age-related macular degeneration (AMD). AMD eye tissues contain high levels of proteins chemically modified by the adduction of oxidation fragments from the long chain polyunsaturated fatty acid, docosahexaenoic acid (DHA). Many proteins modified by these and other adducts are found in drusen and Bruch's membrane. Additionally, autoantibodies against a unique carboxyethylpyrrole (CEP) adduct that can only be generated from DHA are more abundant in the circulation (plasma) of individuals with AMD than in age-matched individuals without AMD.
Methods: Normal mice were immunized with CEP-adducted mouse serum albumin. The prediction was that systemic immunization with CEP would sensitize mice to endogenously generated CEP-adducts produced in the outer retina during the normal course of aging. In turn the immune system would respond by attacking the cells where CEP epitopes are most readily generated. Two immunization protocols were used: one with multiple boosts over a three month period, and the other with a single boost and maintenance of the mice for up to one year post immunization. Eye tissues were recovered and analyzed with microscopy.
Results: In multiple boost mice dramatic lesions of the RPE involving lysis of individual cells are evident along with the invasion of macrophages and debris removal. In single boost animals focal drusen deposits in the fundus were present along with some RPE loss. None of these changes were observed in normal mice immunized with non-adducted mouse serum albumin or when CEP-MSA was used to immunize rag−/− mice that were missing mature T cells and B cells.
Conclusions: Mice immunized with CEP-mouse serum albumin developed changes in the outer retina that are characteristic of those present in humans with AMD. The high concentration of DHA in the photoreceptors-RPE complex coupled and the vulnerability of DHA to oxidative damage resulted in the slow generation of CEP-adducts over time in the outer retina. Normally these CEP-adducts represent new epitopes foreign to the immune system. When mice were immunized with CEP-mouse serum albumin they became sensitized to the CEP-adduct and responded with an immune attack on the cellular source of this adduct the outer retina resulting in these AMD-like changes. This model for AMD in the mouse is an important a new resource for preclinical testing of therapeutics designed to prevent or limit the progression of AMD.

B. Immune Responses to Oxidatively Altered Self Proteins in the Retina Lead to the Development of Retinal Degeneration
Purpose: Patients with Age Related Macular Degeneration (AMD) have circulating auto-antibodies to carboxyethylpyrrole (CEP) modified albumin. CEP adducts are generated in the retinal photoreceptors and RPE in response to oxidative stress. The main goal of this experiment was to determine if the immunization of mice with CEP-modified albumin leads to the generation of an immune response that induces AMD.
Methods: C57BL/6 and Balb/c mice were immunized in the footpad with mouse serum albumin adducted with CEP (CEP-MSA) or non-adducted MSA emulsified in complete Freund's adjuvant (CFA) at day 0. One group of mice was followed for a year and a second group of mice was challenged subcutaneously at day 10 with incomplete Freund's adjuvant-CEP-MSA, followed with a second challenged two months later with CFA-MSA. Clinical examinations of the fundus and electroretinograms (ERG) were performed at different post-immunization times and the appearance of retinal changes were scored. Sera from immunized mice were tested for anti-CEP antibody by ELISA. Mice were sacrificed at different time points for histological examination of enucleated eyes and analysis of T cell priming to CEP in lymph nodes and spleens using Interferon-gamma (IFN-γ) ELISPOT in response to in vitro CEP-MSA stimulation. Rag KO mice were also immunized and challenged.
Results: Mice immunized once developed atrophic retinal changes of the retinal pigmented epithelium (RPE) at 11 months and histological examination showed vacuolization of RPE and patchy areas of loss of photoreceptors consistent with dry AMD. Anti-CEP antibodies were also present at this time point and CEP-MSA specific T cells were readily detected. Mice that were immunized and challenged had increased titers of anti-CEP antibodies at 20 days and detectable CEP-MSA IFN-γ specific T cells in lymph nodes and spleen. Although clinical examination was unremarkable, histological analysis showed significant amount of photoreceptor loss and scattered vacuolization of the RPE. No ERG changes were noted.

Conclusion: Immune responses to a CEP adducted self-protein in the retina can lead to the generation of an adaptive immune response that results in retinal damage consistent with dry AMD. This demonstrates for the first time that an in vivo chemical modification induced by oxidative stress in a specific organ can lead to autoimmunity. Moreover, this represents an animal model to study dry AMD and develop novel therapies.

Discussion

Higher levels of CEP-adducted proteins are present in AMD donor eyes and CEP adducted proteins are present in the blood of AMD patients (Crabb, J. et al, *Proc Natl Acad Sci (USA)* 99:14682-14687 (2002); Hollyfield, J. G., et al., *Adv. Exp. Med. Biol.* 533:83-89 (2003); Gu, X. et al., *J Biol Chem* 278:42027-42035 (2003)). As described herein, whether an immune response to CEP adducted self proteins generated in the retina initiated the development of pathological features associated with AMD was tested. For the antigen, mouse serum albumin (MSA) was chemically modified to generate MSA-CEP (FIGS. 5A-5B) (Gu, X. et al., *J Biol Chem* 278: 42027-42035 (2003)). Aliquots of MSA-CEP were emulsified in complete Freund's adjuvant and C57BL/6 and BALB/c mice were immunized following a previously described immunization regimen (Percopo, C. M., et al., *J Immunol* 145:4101-4107 (1990)).

Two immunization protocols in the development of this mouse model for AMD were used. A short term immunization protocol with two boosts designed as follows:

(A) The short term protocol: Following immunization at day 0 and boosts with incomplete Freund's adjuvant on day 10 and day 60, animals were killed on day 70 and eyes, spleen, lymph nodes and blood were taken for immunological and histological analysis. Control immunizations were with complete Freund's adjuvant alone followed by incomplete Freund's adjuvant at the same intervals as indicated above. Tissues of naïve mice were also used as controls.

(B) The long term protocol: Following immunization on day 0 and a single boost with incomplete Freunds adjuvant on day 10 the mice were maintained for up to one year before being killed, with eyes, blood, spleen and lymph nodes harvested for analysis as described above.

The reasoning in pursuing these two protocols was based on the hypothesis that multiple immunizations would cause a quicker response and possibly involve an attack on the cells in the retina where CEP-adducts were most abundantly generated. In contrast the long term, single boost protocol might result in a slower immune attack on the outer retina with the development of lesions resembling those found in the human AMD condition.

CEP-ELISPOT Assays, T Cell Priming in CEP-Immunized Mice

Standard immunological assays were used to determine whether T cell priming to CEP-MSA had occurred, a phenomenon necessary for T cell dependent B cell response (Parker, D. C., *Ann Rev Immunol* 11:331-360 (1993)). Spleen and lymph nodes were harvested, their cells cultured and tested for the generation of gamma-interferon (IFN-γ) production in response to CEP stimulation using the well established ELISPOT assay. T cells from these tissues with a memory of the CEP antigen respond in culture to stimulation with CEP-MSA by the synthesis of IFN-γ. A color reaction in the cells that produce IFN-γ can be resolved and the number of responding cells can be counted. T cells from naïve mice and mice immunized with native MSA that was not adducted with CEP did not respond. Furthermore cultures stimulated with native MSA did not secrete IFN-γ.

Figure 1A:
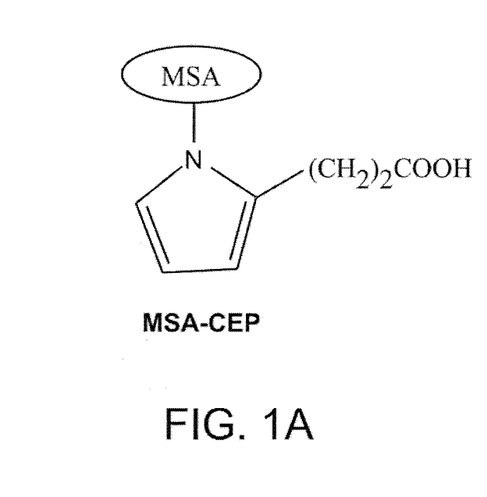
FIG. 1A is the chemical structure of CEP-MSA used to immunize mice.
Figure 1B:
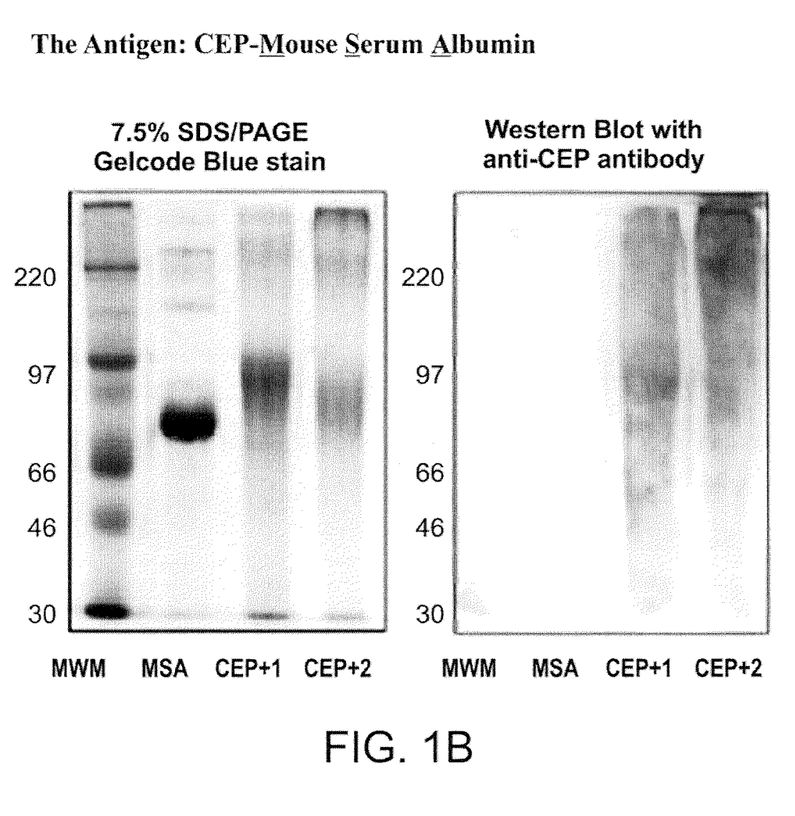
FIG. 1B shows proteins stained with a Gelcode® Blue (Pierce) (left) and by a Western blot (right) prepared using a polyclonal antibody against CEP. Two preparations of CEP-MSA are shown. Both are highly immunoactive to the antibody, but show different mobility in the gel. The pyrrol/protein molar ratios were determined and indicate that CEP-1=11/1; CEP-2=6.6/1. MSA=mouse serum albumin; MWM=molecular weight marker.
Figure 2:
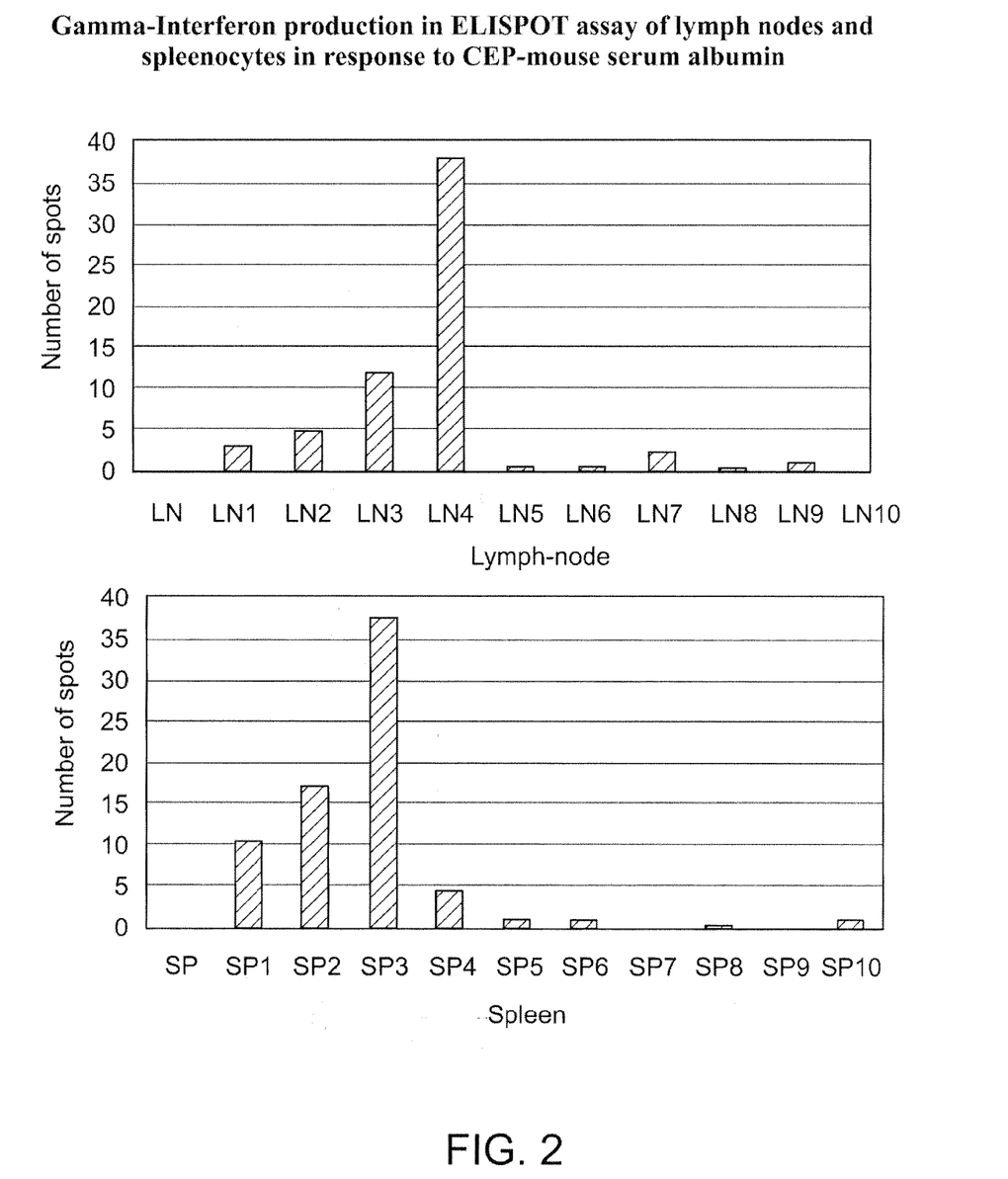
FIG. 2 shows bar graphs of IFN-γ generation in ELISPOT assays of lymph node (left) and spleenic T cells (right) from C57BL/6 mice using the 70 day immunization protocol.

The graphs in FIG. 2 show IFN-γ generation in ELISPOT assays of lymph node (left) and spleenic T Cells (right) from C57BL/6J mice using the 70 day immunization protocol described in the above paragraph. Animals 1-4 were immunized with 200 µg MSA-CEP in complete Freund's adjuvant; animals 5-7 were immunized with complete Freund's adjuvant alone; and animals 8-10 were naive mice. Note that the spleen cells and lymph node T cells in 1-4 responded to CEP-MSA stimulation and cells in 5-10 did not respond.

Anti-CEP Antibody Production in CEP-MSA Immunized Mice

To determine if the CEP-specific T cell responses demonstrated in these mice promoted B cells to produce antibodies against CEP, sera for CEP antibodies were analyzed by ELISA. These assays (FIG. 3) showed circulating anti-CEP antibodies at dilutions as low as 1:500 in the immunized mice, whereas no CEP antibodies were detected in mice immunized with Freund's adjuvant only or in naïve mice. Antibody titers were followed in over 120 mice used in these studies and a range of 2-3 fold variability in the antibody titer was found between animals that are immunized using the same antigen and boost protocols. Non-adducted-MSA immunizations were included as an additional control (not shown).

Figure 3:
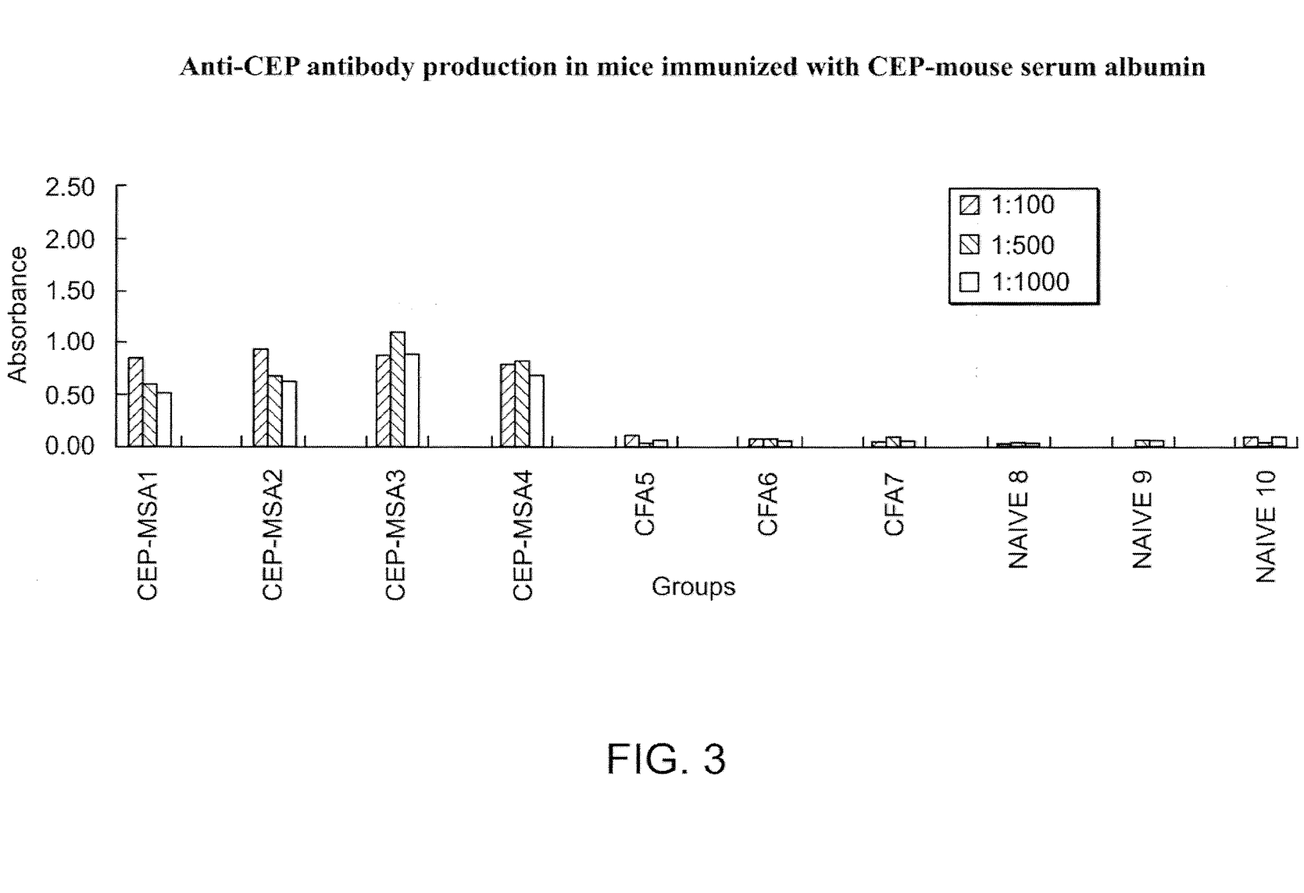
FIG. 3 is a graph of an ELISA analysis for the presence of anti-CEP antibodies in mice immunized with CEP-MSA (1-4), with complete Freund's adjuvant alone (5-7) or in naïve mice (8-10).

The graph in FIG. 3 shows the results of the ELISA analysis for the presence of anti-CEP antibodies in mice immunized with CEP-MSA (1-4), with complete Freund's adjuvant alone (5-7) or in naïve mice (8-10). Note the robust antibody titer (high absorbance levels) at the serum dilutions indicated in 1-4, but the absence of an antibody signal in animals 5-10.

Outer Retina Pathology in the Short Term, Multiple Boost CEP-MSA Immunized Mice

Figure 4A:
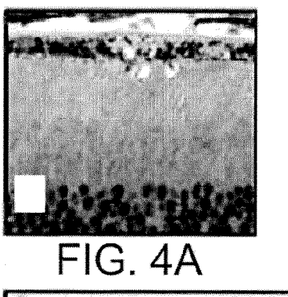
FIGS. 4A-4J show the cryosectioning and immunohistochemistry analysis of outer retinal pathology present in mice immunized with CEP-MSA; large arrows indicate several inflammatory cells immediately adjacent to the RPE or in the IPM; large empty vacuoles are also evident (FIGS. 4C-4I), some of which appear to be intracellular (4I); in 4J the RPE has degenerated (asterisks); bar in lower right of 4J represents 25 μm.
Figure 4B:
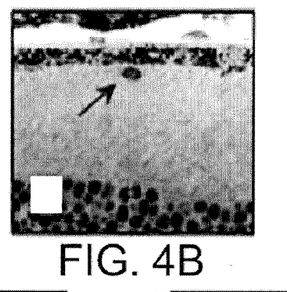
Figure 4C:
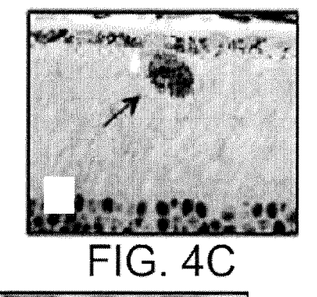
Figure 4D:
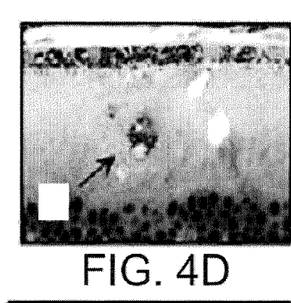
Figure 4E:
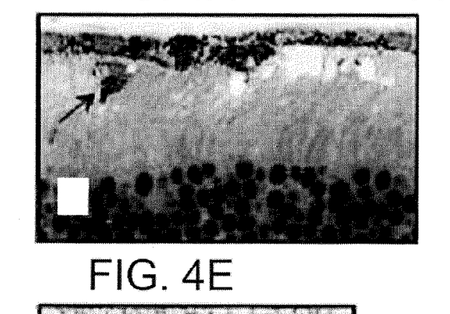
Figure 4F:
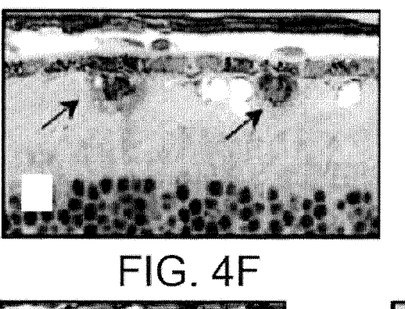
Figure 4G:
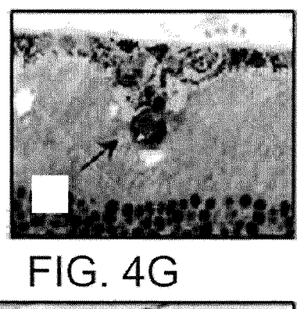
Figure 4H:
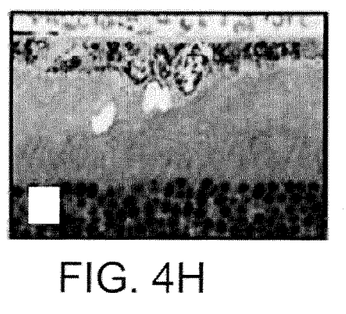
Figure 4I:
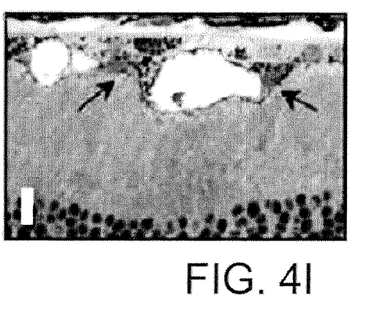
Figure 4J:
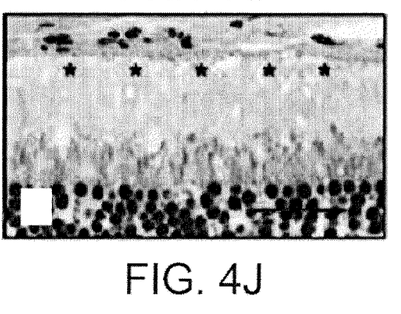

At the time of harvesting, one eye was frozen in OTC (optic tissue compound, O.C.T., Tissue Tek®) for cryosectioning and immuno-histochemistry. The other eye was fixed in mixed aldehydes and embedded in plastic for detailed microscopic analysis as described previously (Besharse, J. C. & Hollyfield, J. G., *Invest. Opthalmol. Vis. Sci.* 18:1019-1024 (1979)). The lesions noted involved the RPE, initially with changes in the distribution of melanin and loss of cytoplasmic staining the cytoplasm (FIG. 4A). In other areas putative inflammatory cells sometimes containing melanin were present adjacent to the RPE in the interphotoreceptor matrix (FIGS. 4B-4I at arrows). Occasional small vesicles could be observed within individual RPE cells (FIGS. 4B-4C), whereas in other areas extensive vesiculation of the entire RPE cell could be observed and in some areas inflammatory cells were noted in close proximity to the RPE lesions. More extensive degeneration was occasionally observed that involved local areas where the entire RPE was missing, producing a condition that was similar to geographic atrophy (FIG. 4J). Photoreceptors under areas of RPE atrophy remained but were highly degenerate in appearance. Some variability was noted in the pathology present in the 35 mice used in these studies. Some have no pathology while others have multiple lesions in the same eye.

Identification of Inflammatory Cells that Invade the Interphotereceptor Matrix (IPM) in CEP-MSA Immunized Mice The identification of the invading cells that move into the outer retina and are associated with the RPE lesions have been examined with a number of specific inflammatory cell markers. Using a marker for macrophages (F4/80 from eBiosciences, San Diego) it was shown that some of the cells that move into the outer retina are indeed macrophages since they are decorated with the F4/80 antibody (FIGS. 5A-5D).

Figure 5A:
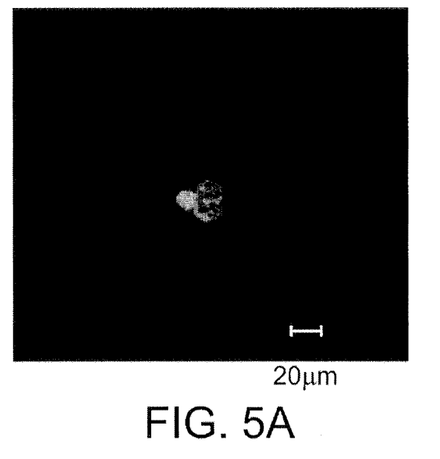
FIGS. 5A-5D show confocal, phase contrast and merged images of F4/80 immunocytochemistry of frozen tissue recovered from a short term (multiple boost) CEP-MSA immunized mouse.
Figure 5B:
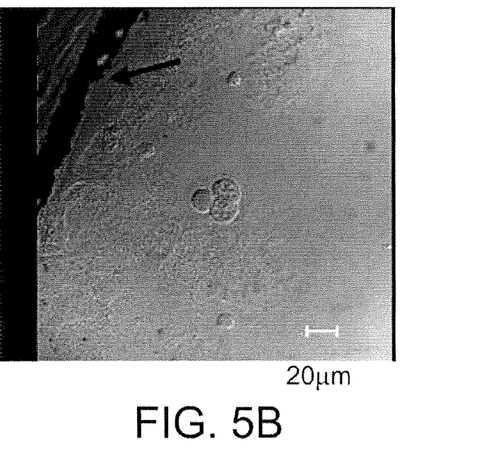
Figure 5C:
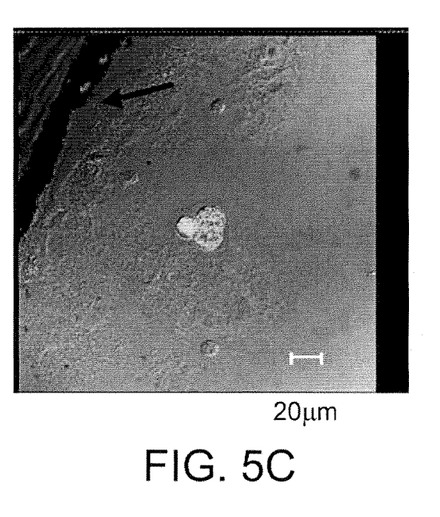
Figure 5D:
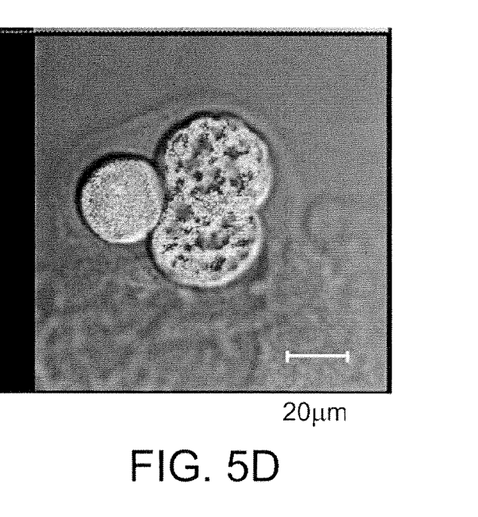

In FIGS. 5A-5D, confocal, phase contrast and merged images of F4/80 immunocytochemistry of frozen tissue recovered from a short term (multiple boost) CEP-MSA immunized mouse are shown. The images presented are from the same animal as the fixed tissue image presented in FIG. 4G. FIG. 5A is a low magnification confocal image showing three F4/80 positive cells. FIG. 5B is a phase contrast image showing the localization of these cells in the outer retina (arrow shows location of RPE/choroid). FIG. 5C is a merged image of 5A and 5B. It should be noted that the retinal structure is not maintained well when the mouse eye is frozen. FIG. 5D is a higher magnification of the three F4/80 positive macrophages. The cell on the left has uniformly staining cytoplasm whereas the two on the right have vesicles in the cytoplasm that are unstained with the antibody. Some of these profiles appeared to be melanin, similar to what was observed in many of the images presented in FIGS. 4A-4J.

Interpretation of the Data from the Short-Term Immunization Protocol

The above data show that CEP-MSA immunized C57BL/6 mice develop CD4 T helper cell responses to CEP necessary for the elaboration of anti-CEP antibodies. These antibodies may be involved in the deposition of C3 in Bruch's membrane and the choroid of the immunized mice. In the retina, RPE lysis and cell death are closely associated with a small number of inflammatory cells in the IPM (subretinal space). Some of these inflammatory cells are identified as macrophages based on their labeling with the macrophage marker F4/80 antibody. The focal loss of RPE resembles a condition of AMD referred to as geographic atrophy, the end stage of the dry form of AMD. The retinal cell type targeted by the immune system in this short-term, multiple boost immunization protocol is the RPE, which consistently shows focal changes in multiple sites in the fundus of the eye.

Outer Retina Pathology in the Long-Term, Single Boost CEP-MSA Immunized Mice

Eighteen (18) mice from the long-term protocol that were maintained for 12 months following immunization with CEP-MSA were examined. Serum samples from each of the animals contained a high titer of anti-CEP antibodies, indicating the successful immunization with MSA-CEP 12 months earlier. Eye tissues and blood from naïve mice, mice that were immunized with non-CEP adducted MSA (normal MSA) and mice immunized with only Freund's complete adjuvant were also recovered. No evidence for anti-CEP antibodies was found in the serum from these control mice. Detailed histology was performed on all of these samples and electron microscopy on representative tissues. In all the CEP-MSA immunized mice many features of dry AMD present in the outer retina were observed. Focal areas in the fundus contain sub-RPE deposits that resemble both soft drusen (FIG. 6A) when compared to soft drusen in human AMD tissue samples (FIG. 6B). Also observed are focal deposits that elevate the RPE and resemble hard drusen (FIG. 6C).

Figure 6A:
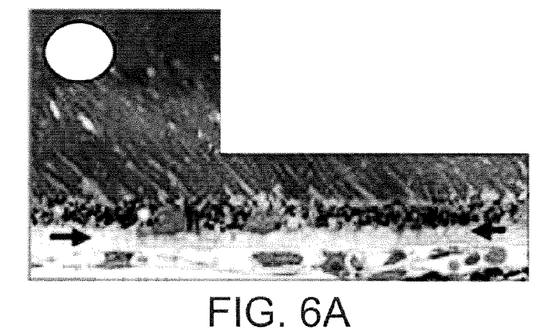
Figure 6B:
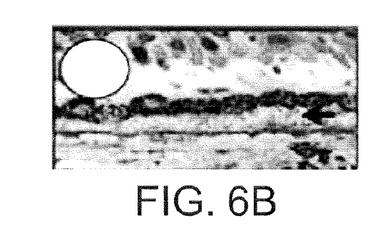
Figure 6C:
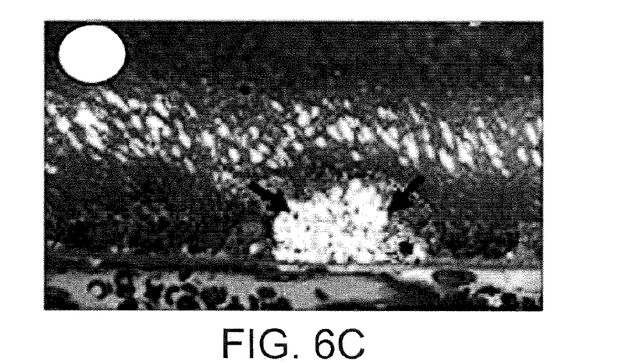

FIGS. 6A-6C show micrographs of retina from mice (FIG. 6A and FIG. 6C) recovered 12 months following immunization with CEP-MSA in complete Freunds adjuvant (FA) followed by a boost 10 days after the initial immunization with CEP-MSA in incomplete FA. In FIG. 6A, arrows on the lower border of the micrograph indicate the localization of debris-like material present below the RPE. FIG. 6B is from a 78 year old human female AMD donor eye containing soft drusen between the RPE and Bruch's membrane (at the level of the arrow on right of image). Compare the sub-RPE material in FIG. 6A with that in FIG. 6B. In FIG. 6C the RPE is elevated over a focal deposit resembling hard drusen that contains vesicular material (arrows). Because of the highly localized position of this material, it resembles hard drusen in human AMD tissues.

Figure 7A:
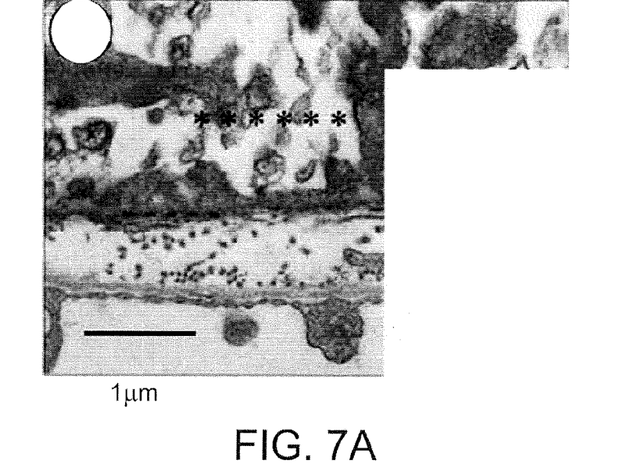
FIGS. 7A-7B show electron microscopy results from the basal side of the RPE at the level of Bruch's membrane.
Figure 7B:
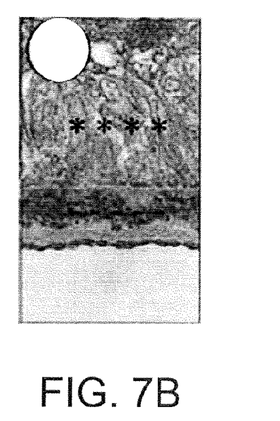
Figure 8:
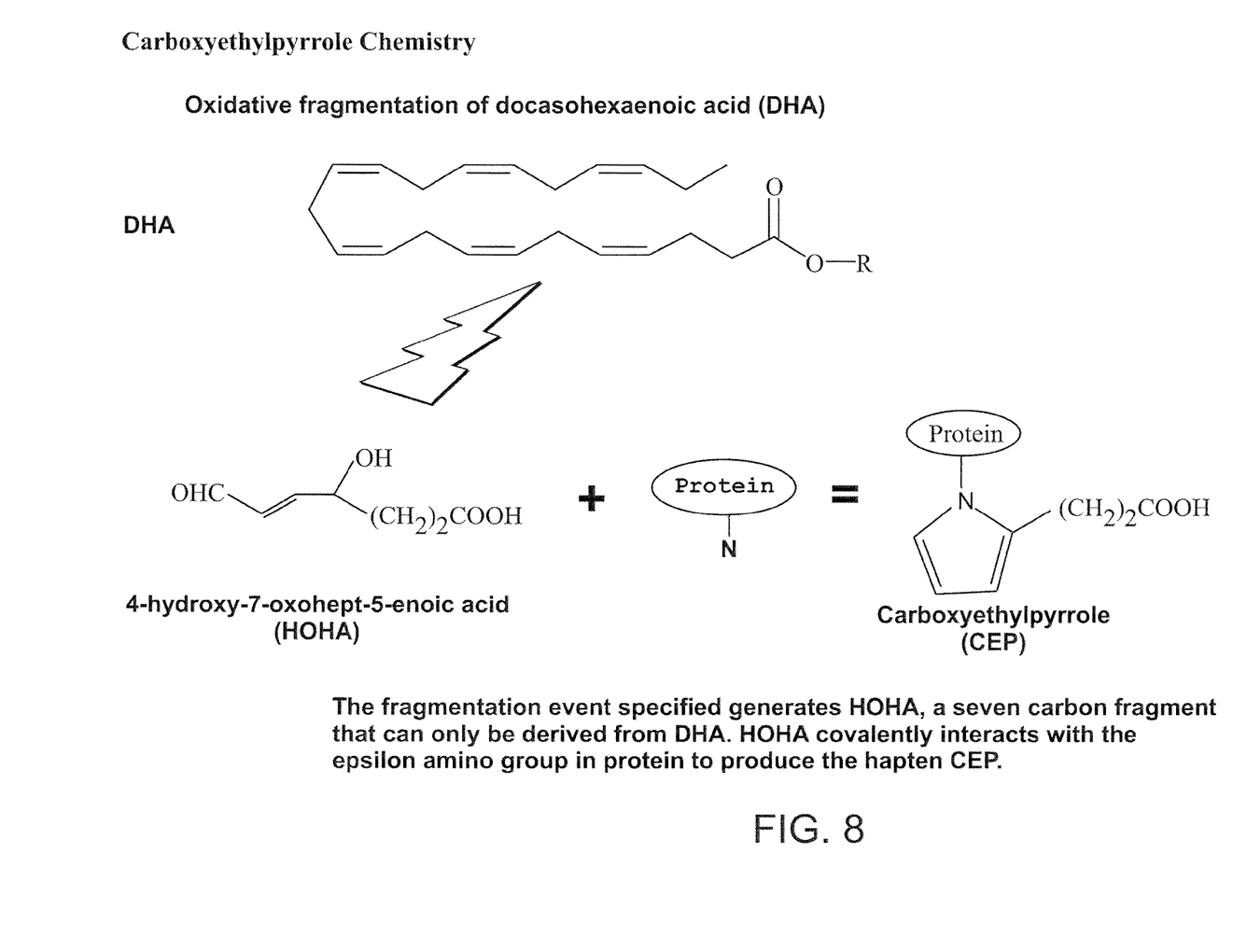
FIG. 8 is a schematic of carboxyethylpyrrole chemistry; the fragmentation event specified generates HOHA, a seven carbon fragment that can only be derived from DHA; HOHA covalently interacts with the epsilon amino group in protein to produce the hapten CEP.

Electron microscopy of these sub-RPE deposits show that much of this material consists of membrane and cytoplasmic debris that may have originated from the basal side of the RPE. When these sub-RPE deposits were observed, the basal infoldings of the RPE were absent and the inner collagenous layer of Bruch's membrane and the basal lamina of the RPE could not be distinguished (FIGS. 7A-7B). None of these changes were observed in the control mice. The data presented clearly indicate that the initial hypothesis is correct: mice immunized with CEP adducted to a self protein, MSA, will be sensitized to CEP adducts generated in the outer retina where the parent molecule, docosahexaenoic acid (DHA), is present in high concentrations and this tissue interface of the outer retina will undergo pathological changes similar to those that occur in AMD.

FIGS. 7A-7B show electron microscopy (EM) results from the basal side of the RPE at the level of Bruch's membrane. FIG. 7A shows sub-RPE material (asterisks) shows high electron density deposits surrounded by electron lucent areas suggesting edema. FIG. 7B is from a control mouse showing the normal appearance of the basal infoldings of the RPE (asterisks). Dashed lines in both figures represent the level of the central elastin lamina of Bruch's membrane. In FIG. 7A, Bruch's membrane is greatly swollen when compared to the control in 7B, and lamina proximal to the RPE are absent. FIGS. 7A and 7B are presented at the identical magnifications.

Interpretation of the Data from the Long-term, Single Boost CEP-MSA Immunization Protocol The long-term immunization protocol clearly shows the development of sub-RPE deposits that resemble soft drusen present in AMD in humans. Normally the high concentration of DHA in the photoreceptors-RPE complex coupled with the vulnerability of DHA to oxidative damage results in the slow generation of CEP-adducts over time in the outer retina. These CEP-adducts represent new epitopes foreign to the immune system and may cause a low grade inflammation. When mice are immunized with CEP-mouse serum albumin using the multiple boost protocol they become sensitized to the CEP-adduct and respond with an immune attack on the cellular source of this adduct the outer retina resulting in these AMD-like changes. In the single boost protocol, a slower inflammation proceeds accompanied by drusen accumulation below the RPE that is strikingly similar to deposits present in dry AMD in humans. Using CEP-MSA, a model for the human AMD disease has been created. This mouse model for AMD is an important new resource for preclinical testing of therapeutics designed to prevent or limit the progression of AMD.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of producing a mouse having one or more pathological characteristics of retinal degeneration comprising:

a) subcutaneously administering to a mouse a composition comprising an adjuvant and a carboxyethylpyrrole (CEP) adducted mouse serum albumin to produce antibodies against CEP; and b) maintaining the mouse of step (a) under conditions in which one or more pathological characteristics of retinal degeneration develops in said mouse, wherein one or more pathological characteristics of retinal degeneration is selected from the group consisting of lysis of retinal pigmented epithelium (RPE) cells, the presence of invading inflammatory cell in the interphotoreceptor matrix (IPM), and focal loss of RPE, thereby producing mouse having one or more pathological characteristics of retinal degeneration.

2. The method of claim 1, wherein the mouse is administered multiple doses of the composition.

3. The method of claim 2, wherein the mouse is administered the composition on day 0, day 10 and day 60.

4. The method of claim 2, wherein the mouse is administered the composition on day 0 and on day 10.

5. The method of claim 1, wherein the adjuvant is selected from the group consisting of: complete Freund's adjuvant (CFA) and incomplete Freund's adjuvant (IFA).

6. The method of claim 5, wherein the adjuvant is complete Freund's adjuvant (CFA) and incomplete Freund's adjuvant (IFA).

7. The method of claim 5, wherein the adjuvant is complete Freund's adjuvant (CFA).

\* \* \* \* \*

UNITED STATES PATENT AND TRADEMARK OFFICE
CERTIFICATE OF CORRECTION

| | |
|---|---|
| PATENT NO. | : 8,664,470 B2 |
| APPLICATION NO. | : 12/256274 |
| DATED | : March 4, 2014 |
| INVENTOR(S) | : Victor L. Perez, Joe G. Hollyfield and Robert G. Salomon |

It is certified that error appears in the above-identified patent and that said Letters Patent is hereby corrected as shown below:

Title Page, Col. 2, item (56) line 16, delete "Seqments" and insert -- Segments --

Signed and Sealed this
Twenty-sixth Day of January, 2016

Michelle K. Lee
*Director of the United States Patent and Trademark Office*